United States Patent [19]

Spasiano et al.

[11] 3,955,581

[45] May 11, 1976

[54] THREE-STAGE SURGICAL INSTRUMENT

[75] Inventors: Anthony D. Spasiano, Old Greenwich; Douglas G. Noiles, New Canaan, both of Conn.

[73] Assignee: United States Surgical Corporation, New York, N.Y.

[22] Filed: Oct. 18, 1974

[21] Appl. No.: 516,112

[52] U.S. Cl. ............................................. 128/334 R
[51] Int. Cl.² ............................................. A61B 17/04
[58] Field of Search ................ 72/407; 128/334 R; 227/19

[56] References Cited
UNITED STATES PATENTS

| | | | |
|---|---|---|---|
| 3,519,187 | 7/1970 | Kapitanov et al. | 128/334 R X |
| 3,638,847 | 2/1971 | Noiles et al. | 227/19 |
| 3,740,994 | 6/1973 | DeCarlo, Jr. | 72/407 |
| 3,819,100 | 6/1974 | Noiles et al. | 227/19 |
| 3,844,289 | 10/1974 | Noiles | 128/334 R |

*Primary Examiner*—Channing L. Pace
*Attorney, Agent, or Firm*—Fleit & Jacobson

[57] ABSTRACT

A surgical instrument for controlling the operation of a three-stage staple-carrying cartridge adapted to ligate, suture and divide organic tubular structures such as blood vessels. The instrument also operates in three-stages to positively control the ligating, suturing and dividing operations of the cartridge. The cartridge actuating mechanism takes the form of three saddles which are in turn controlled by the operating mechanism of the instrument. A two-link mechanical toggle positively controls the operation of two of the three cartridge-actuating saddles. The third saddle is, in turn, controlled by a shifter dog mechanism. The instrument is also equipped with a mechanism which ensures the completion of a ligating, suturing and dividing cycle to avoid jamming the staple-carrying cartridge.

20 Claims, 9 Drawing Figures

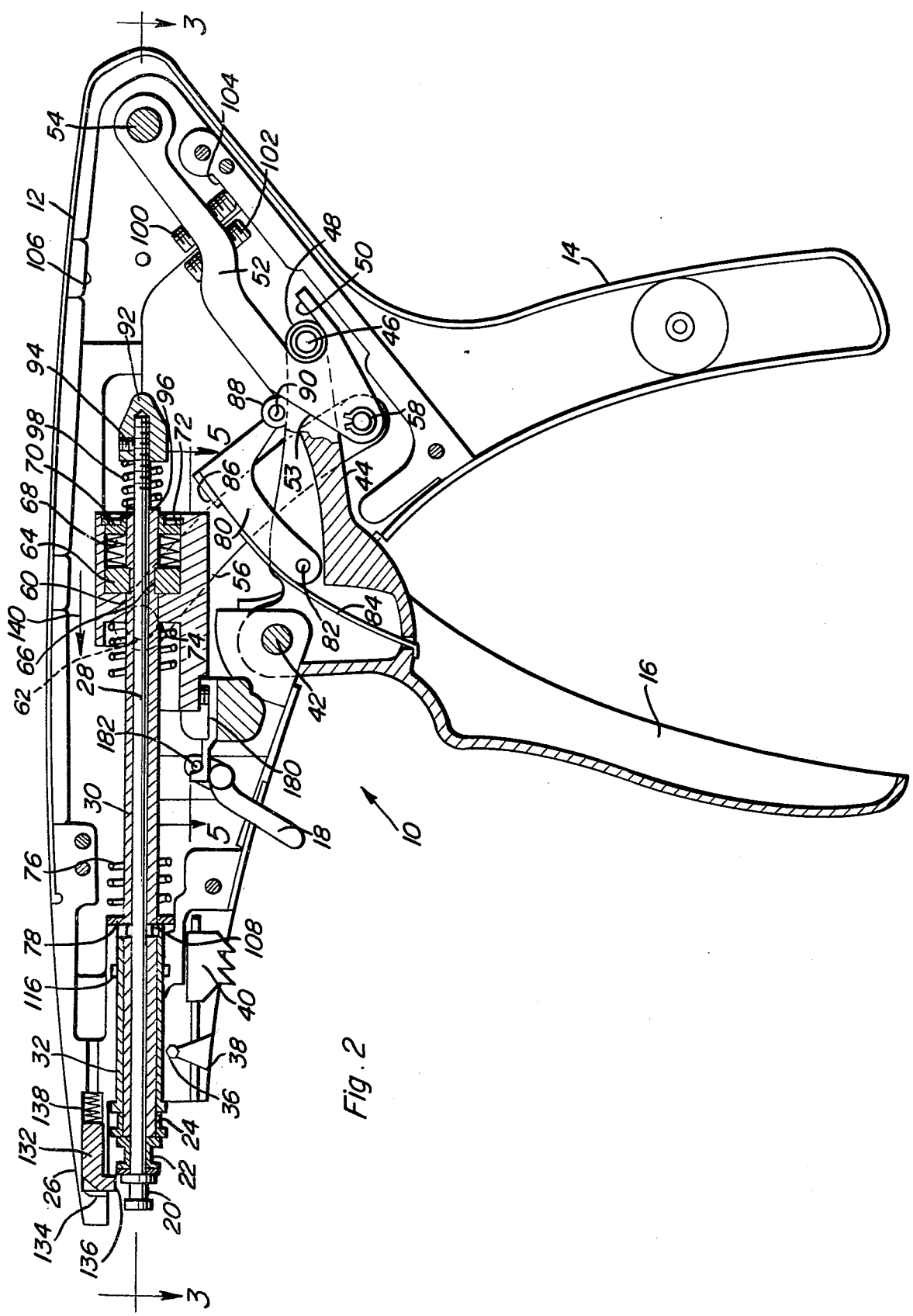

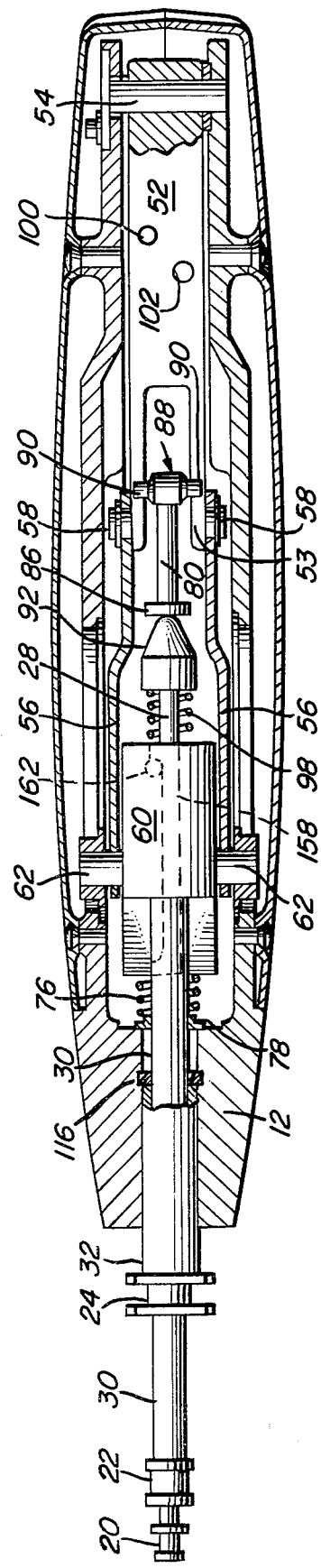
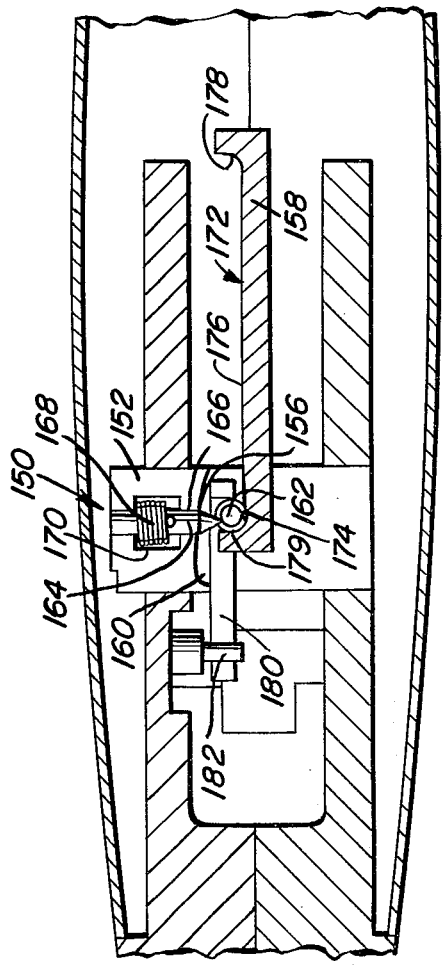
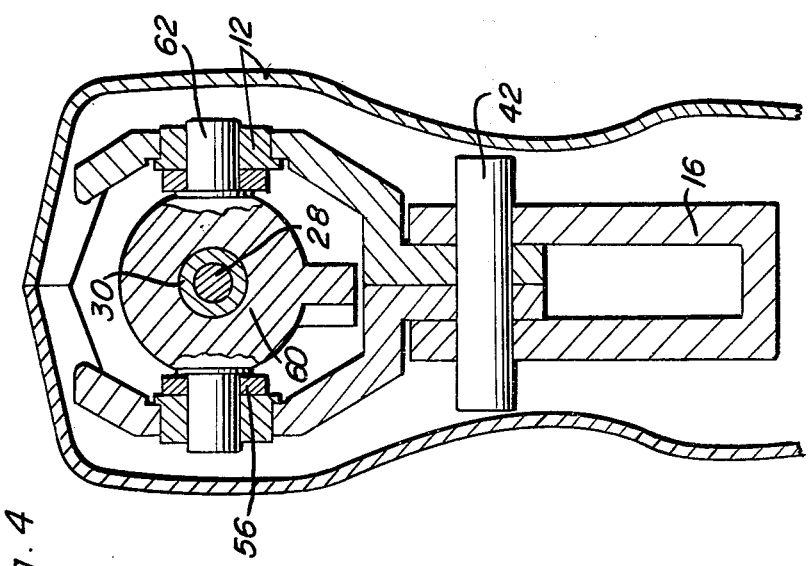
Fig. 3
Fig. 5
Fig. 4

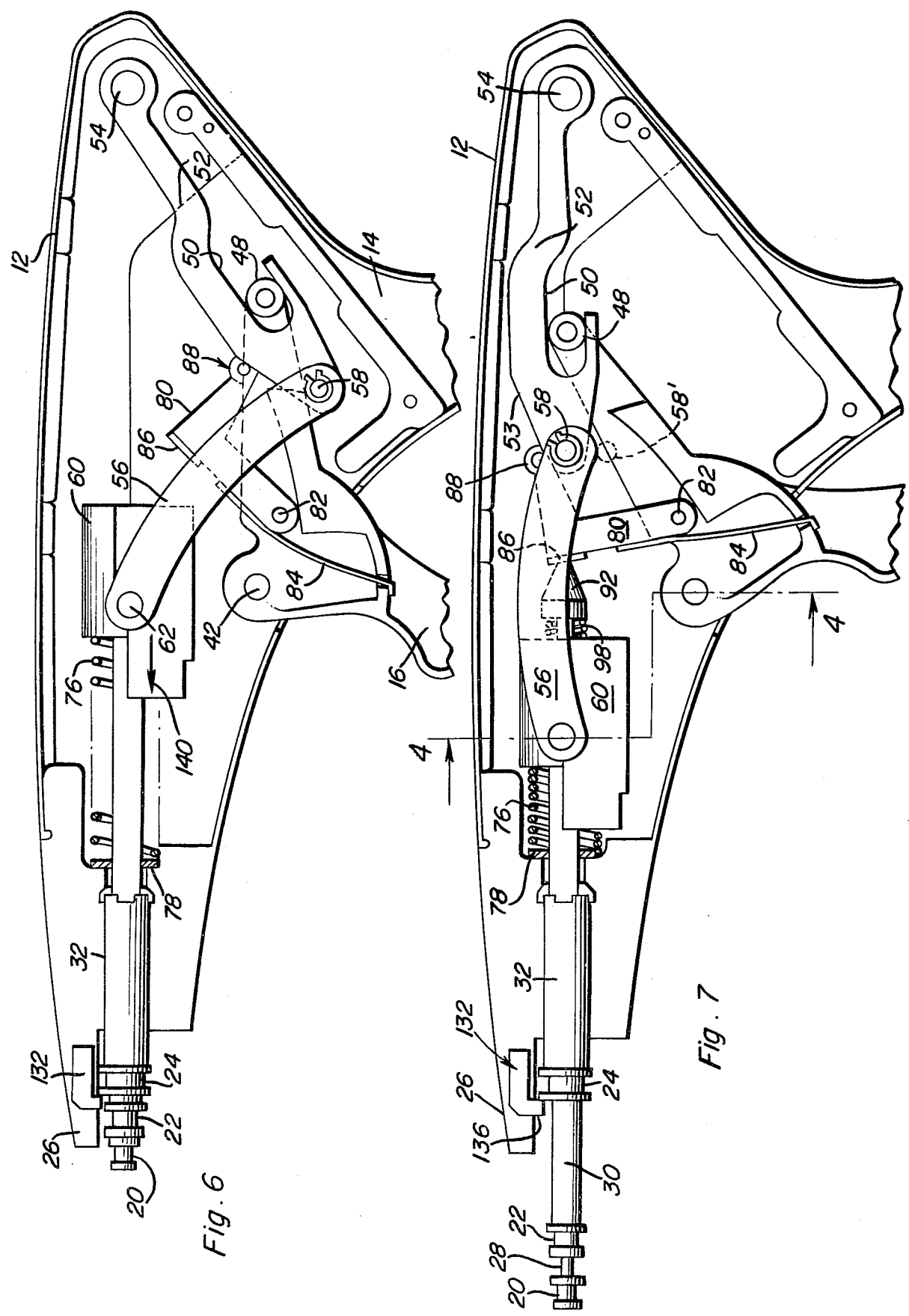

THREE-STAGE SURGICAL INSTRUMENT

BACKGROUND OF THE INVENTION

In U.S. Pat. No. 3,740,994, assigned to the present assignee and entitled Three-Stage Medical Instrument, a novel cartridge and instrument for ligating, suturing and dividing organic tubular structures by means of surgical staples are disclosed. The present invention relates to an instrument which, together with a cartridge such as disclosed in the commonly assigned patent, is similarly capable of mechanically and repetitiously ligating, suturing and dividing organic tubular structures, such as blood vessels and the like.

The instrument of the present invention is adapted to associate with a cartridge which operates in three stages such as disclosed in the commonly assigned patent. Once the tubular structure is inserted within the area of its jaws, the cartridge wrap, or main body of the cartridge, is moved forward and toward an anvil assembly fixed on the instrument, thereby enclosing the tubular structure within the jaws of the cartridge. Then, a pair of pusher elements is advanced along respective fixed rail assemblies and urge a pair of staples toward respective anvil assemblies. At the forward portion of the pusher stroke, the respective staples encircle the tubular structure at spaced locations and crimp about the structure in such a manner that the tubular structure is sealed at two locations. Finally, and with the pushers at the forwardmost portions of their strokes, a knife blade advances and divides the tubular structure intermediate the two staples.

The instrument disclosed in the commonly assigned patent is also of three-stage design. The forward end of the instrument is provided with three saddles which associate, respectively, with the cartridge wrap, the pushers and the knife of the three-stage cartridge. Three spring elements are housed in the instrument and, in conjunction with a trigger element, operate the cartridge wrap, the pushers and the knife through the three saddle elements. With a cartridge mounted on the instrument, the initial squeezing of the handle moves the cartridge wrap toward the fixed anvil assemblies, and the further squeezing overcomes the force exerted by one of the springs and advances the pushers toward the respective anvils and ultimately, after overcoming the force exerted by another of the springs, urges the knife toward the front of the instrument to effect a cutting operation.

Because of the three-stage operation which depends upon the interaction of three biasing springs, the forces which need to be exerted on the handle of the instrument of the commonly assigned patent are large, and vary with the handle depression. Further variance in the required operating forces is caused by the distinct operations of the cartridge. To eliminate the distance "feel" in the hand of the surgeon that differential forces are required of him, the instrument disclosed in the commonly assigned patent is provided with a variable cam element operating between the power shafts of the instrument and the handle thereof. The cam surface is contoured in such a manner that the force required to operate the handle is relatively constant notwithstanding variations in the required force inputs to the cartridge. In this manner, the surgeon is unaware that three distinct stages of operation occur each time he actuates the instrument.

While the known surgical instrument described in the commonly assigned patent operates satisfactorily, there is room for improvement, particularly with respect to the spring biasing of the saddles.

It is accordingly one object of the present invention to provide a surgical instrument which overcomes the problems of the prior surgical instruments which are noted above.

Yet another object of the present invention is to provide a three-stage surgical instrument adapted to associate with a cartridge and to function, together with the cartridge, to ligate, suture and divide tubular organic structures.

Yet a further object of the present invention is to provide a simple hand-operated instrument adapted for three-stage operation without the necessity for overcoming large spring biases.

A further object of the present invention is to provide a surgical instrument having a simple mechanical linkage which positively controls the operation of a three-stage staple-carrying cartridge.

Still another object of the present invention is to provide a surgical instrument which makes effective use of the mechanical advantage developed by a simple linkage mechanism for controlling the operation of a staple-carrying cartridge.

Yet another object of the present invention is to provide a surgical instrument wherein relative movement between cartridge control elements is provided without biasing springs by means of a shifter dog arrangement.

These and other objects of the present invention, as well as many of the attendant advantages thereof, will become more readily apparent when reference is made to the following description taken in conjunction with the accompanying drawings.

SUMMARY OF THE INVENTION

The present invention relates to a hand-held three-stage surgical instrument for associating with a staple-carrying cartridge adapted to ligate, suture and divide organic tubular structures. The inventive instrument is simple, and yet effective, and eliminates numerous of the disadvantages common to prior art medical instruments.

The operation of a staple-carrying cartridge associated with the inventive medical instrument is controlled through the means of three saddle elements. One of the saddle elements, controlling the pusher, is in direct mechanical association with a trigger operable by the surgeon. One of the remaining saddle elements, controlling the wrap, is operable in response to the position of the trigger-controlled saddle element, through the means of a novel coupling arrangement. The third saddle element, controlling the knife of the cartridge, is actuated by a linkage whose operation is controlled directly by the trigger. In this manner, the drawbacks associated with the prior art multiple biasing springs are avoided.

The trigger of the inventive surgical instrument operates a simple two-element mechanical linkage and derives maximum benefit from the mechanical advantage developed thereby. During the initial stages of operation, when the cartridge wrap closes over the associated organic tubular structure, the relatively small mechanical advantage developed by the inventive linkage is sufficient. Then, as the mechanical advantage of the inventive linkage increases, the pushers advance their associated staples along the rail assemblies of the cartridge toward the anvil. Again, this relatively small mechanical advantage is sufficient. At the time when the staples are being crimped about the organic tubular structure to suture the same, it is necessary that substantial forces be developed. It is at this point in time that the inventive mechanical linkage develop maximum mechanical advantage. Accordingly, without the necessity for complex camming arrangements, the inventive surgical instrument transforms the relatively small force on squeeze exerted by the surgeon into the substantial forces required to crimp staples about a tubular structure. At the final operating stage, the inventive medical instrument advances the knife of the cartridge to divide the already sutured organic tubular structure. The knife is advanced by a simple actuating lever which is controlled directly by the two-element mechanical linkage. The linkage associates with the cartridge knife in such a manner that during this operating stage, the movement in the knife is substantial, while the movement of the remaining elements in the instrument is small.

BRIEF DESCRIPTION OF THE DRAWINGS

FIG. 2 is a cross-sectional view of the instrument illustrated in FIG. 1, showing the instrument in its relaxed state;

FIG. 3 is a cross-section of the inventive instrument taken along line 3—3 of FIG. 2, but showing the instrument near the end of the third operating stage;

FIG. 4 is a cross-section of the inventive instrument taken along line 4—4 of FIG. 7;

FIG. 5 is a cross-section of the inventive instrument taken along line 5—5 of FIG. 2;

FIG. 6 is an enlarged view of the inventive instrument, but illustrating the instrument at the end of the first operating stage;

FIG. 7 is an enlarged view similar to FIG. 6, illustrating the inventive instrument near the end of the third operating stage;

DETAILED DESCRIPTION OF THE INVENTION

Figure 1:
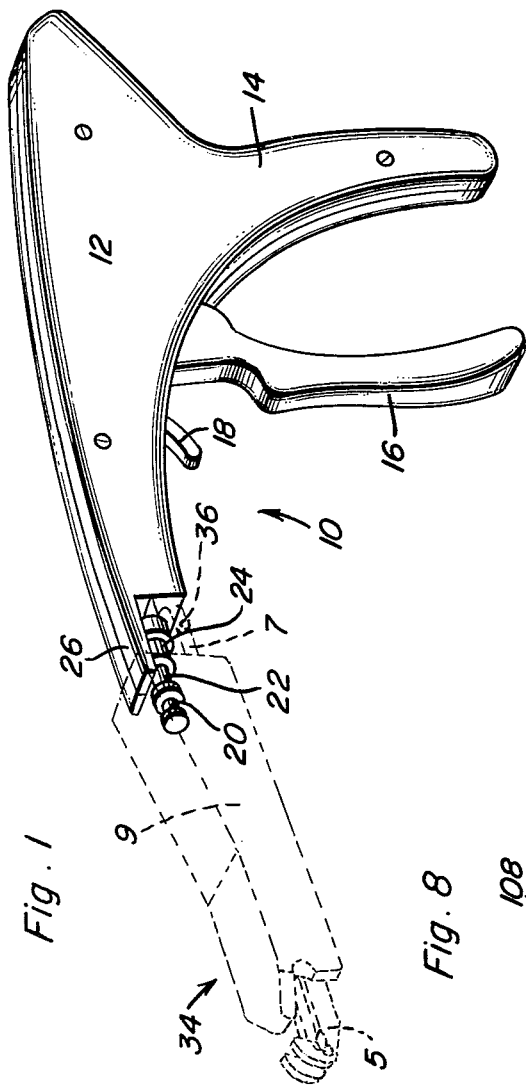
FIG. 1 is a perspective view of the inventive surgical instrument as it associates with a staple-carrying cartridge.

Referring first to FIG. 1, the general configuration of the inventive surgical instrument will be described. The instrument is shown generally at 10 and comprises a main body portion 12, a handle 14 and a trigger 16. A clutch release trigger 18 can also be seen forward of main trigger 16. As seen best in FIg. 2, saddles 20, 22, and 24 extend from the nose 26 of the instrument 10. For reasons which will become clear from the following paragraphs, saddle 20 is integral with a knife rod 28, saddle 22 with pushers sleeve 30 and saddle 24 with wrap sleeve 32.

A staple-carrying cartridge 34 is mounted on the nose 26 of the instrument 10 as illustrated in FIG. 1, cartridge 34 includes a set of anvil assemblies 5 integral with rails 7 which are fixed to the instrument 10, and a cartridge wrap 9 moveable on rails 7 so as to close about a vessel in the jaws of the cartridge. As noted above, the cartridge 34 carries out three operations. First, after the vessel to be sutured and divided is placed within the jaws of the cartridge 34, the jaws are closed so as to capture the vessel between the anvils 5 and the wrap 9. Then, a pair of staples is urged toward respective anvils by a pair of pusher elements, and crimped to ligate the vessel at spaced locations along the length of the vessel. Finally, once the stapling operation is completed, a knife located intermediate the two staples advances and divides the twice sutured vessel. The inventive instrument 10, through its saddles 20, 22 and 24 and associated mechanisms, effects such a three-stage operation of the cartridge as that described above.

As best seen in FIG. 2, the rails 7 are fixed relative to the instrument 10 by way of interaction between a pin 36 through the rails of the cartridge and a groove 38 at the bottom of the instrument. Once the pin 36 of the cartridge 34 is resting at the bottom of groove 38, then a finger-operated latching mechanism 40 is moved to cover the groove 38 and hence to latch the cartridge in place. When in this position, the wrap 9 of the cartridge 34 is controlled by way of saddle 24. The pushers in the cartridge which advance and bend the staples are controlled by way of saddle 22. The knife which divides the sutured vessel is controlled by saddle 20. The anvil assemblies 5, it will be recalled, are fixed relative to the instrument.

With continuing reference to FIG. 2, the trigger 16 is pivotally mounted to the main body 12 by means of a pivot pin 42. The opposite end of the trigger 16 defines a bell crank 44 at the most rearward portion of which is a pin 46 supporting a pair of rollers 48. The rollers 48 of the bell crank 44 are positioned within a recess 50 defined in a rear link 52. The rear link 52 is pivotally mounted to the main body 12 by way of a pin 54. A forward link 56 is pivotally connected to the rear link 52 by way of a pivot pin 58. The forward link 56 is pivotally connected to a thrust block 60 by way of a pin 62. As best seen in FIG. 3, the forward end of the rear link 52 defines a yoke which associates with two separate pins 58. Similarly, the forward link 56 takes the form of two separate link members pinned to the thrust block 60 by way of two separate pins 62.

Again, with reference to FIG. 2, the thrust block 60 is yieldably fixed relative to sleeve 30 by a retainer 64 which seats in a recess 66 defined at the rear portion of the pushers sleeve 30. For reasons which will become clear from the following, a set of Bellville spring washers 68 are located within a hollow in the thrust block 60 and are retained between retainer 64 and a retainer washer 70 held in place by a snap ring 72. An abutment surface 74 is defined in a hollow at the forward end of the thrust block 60 and serves as a seat for a return spring 76, the forward end of which abuts against a washer 78 restrained by the main body 12.

A knife actuating lever 80 is pivotally mounted to the trigger 16 by way of a pin 82. A spring 84 biases the knife actuating lever 80 into the position illustrated in FIG. 2. At the forward end of lever 80 is a contact pad 86, and at the rearward end of lever 80 is a cam follower 88 in the form of a cylinder having projecting surfaces 90 which are adapted to be guided by the camming surface 53 of rear link 52. This is best seen in FIG. 3.

The rearward most end of the knife rod 28 is threaded, and associates with a threaded follower 92 which is held in place by way of a set screw 94. The end 96 of pusher sleeve 30 serves as a retainer for a knife return spring 98. As best seen in FIG. 2, knife return spring 98 develops a biasing force which urges saddles 20 and 22 toward one another.

A pair of set screws 100 and 102 are threadably secured in the rear portion of rear link 52. In the position illustrated in FIG. 2, set screw 100 abuts a stop 104 to limit the counterclockwise rotation of the rear link 52. Set screw 102, on the other hand, is adapted to abut a stop 106 to limit the clockwise rotation of the rear link 52. In this regard, it should be noted that the return spring 76 maintains the instrument in the relaxed position illustrated in FIG. 2. Clockwise rotation of the rear link 52 is effected by actuating the trigger 16 as will later be described when reference is made to FIGS. 6 and 7.

Figure 8:
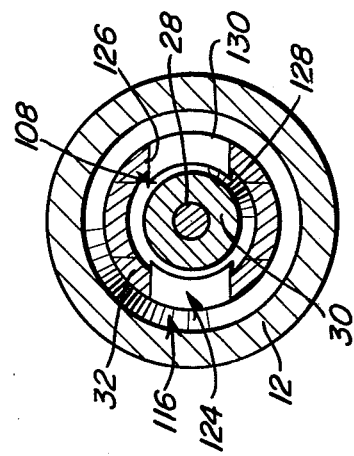
FIG. 8 is an end view of the cartridge actuating mechanism employed in the inventive instrument.
Figure 9:
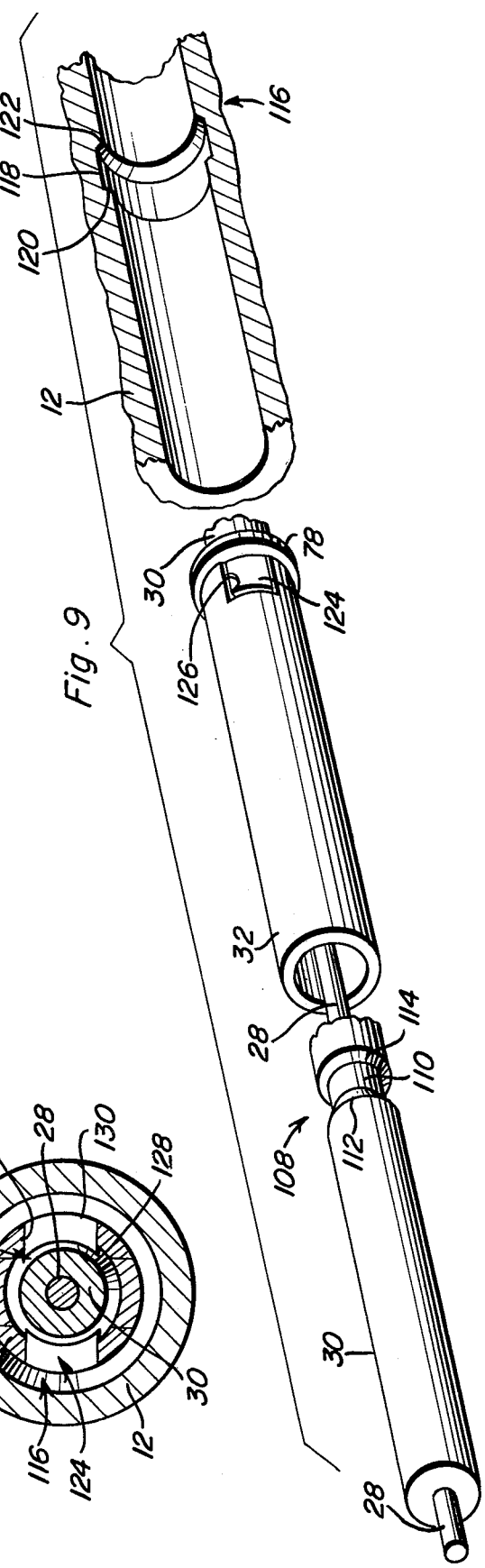
FIG. 9 is an exploded perspective view of the mechanism illustrated in FIG. 8.

As noted above, one characteristic feature of the inventive stapling instrument is that certain of the biasing springs common to known instruments have been eliminated. With reference now to FIGS. 2, 8 and 9, the mechanism by which such biasing springs are eliminated will be described. An annular channel 108 is formed in the outer surface of pusher sleeve 30. Channel 108 has a cylindrical base 110 and a pair of opposite tapered walls 112 and 114. A complementary channel 116 is defined in a wall of the main body 12. Annular channel 116 is defined by a cylindrical base 118 and a pair of tapered side walls 120 and 122. It should be appreciated that while walls 112 and 120 are illustrated as being tapered, these walls could be normal to their respective bases 110 and 118.

The wrap sleeve 32 slides over the pusher sleeve 30 and has a pair of shifter dogs 124 associated therewith. Shifter dogs 124 are on diametrically opposite sides of the hollow wrap sleeve 32 and are mounted in respective windows 126 to move radially relative to the wrap sleeve 32. As can best be seen in FIG. 8, the shifter dogs 124 have cylindrical inner and outer faces 128 and 130, respectively. The respective shifter dogs 124 designed so as to slide radially within their windows 126 and extend either into channel 108 in the pusher sleeve 30 or into channel 116 integral with main body 12. Therefore, the shifter dogs serve the function of coupling wrap sleeve 32 to either the pusher sleeve 30 or the main body 12.

Also related to the operation of the shifter dog mechanism described above is a stop 132 mounted in the nose 26 of the instrument 10. As best seen in FIG. 2, the stop 132 is positioned in a recess 134 defined in the main body 12. A nose portion 136 of the stop 132 extends toward the saddles, and is positioned so as to serve as an abutment for saddle 24 to limit the forward motion of saddle 24 and its associated wrap sleeve 32. A spring 138 is housed in the recess 134 behind the stop 132.

Turning now to FIG. 5, there is illustrated a top view of a clutch mechanism 150. Clutch mechanism 150 includes a cam block 152 mounted below thrust block 60. Cam block 152 cooperates with thrust block 60 and has an inclined surface 156 facing thrust bar 158. Inclined surface 156 is positioned relative to thrust bar 158 such that the spacing 160 between inclined surface 156 and thrust bar 158 defines an opening whose dimensions increase in the forward thrust direction of the thrust bar. A cylindrical cam roller 162 is positioned between inclined surface 156 of cam block 152 and thrust bar 158. An elongated wedge pin 164 is housed in an aperture 166 in cam block 152. The forward end of pin 164 is V-shaped and extends into opening 160 between inclined surface 156 and thrust bar 158. The wedge pin 164 is spring-biased toward thrust bar 158 by means of a spring 168 housed in a recess 170 in cam block 152. Cam roller 162 lies adjacent elongated notch 172 in thrust bar 158 and its movement is confined by notch 172. The cooperation between these elements is such that cylindrical roller 162 prevents thrust bar 158 from being returned to its relaxed position until completion of a full thrust stroke.

Thrust bar 158 is shown in its relaxed position in FIG. 5. In this position, cam roller 162 lies in a shallow cut-out 174 positioned at the forwardmost end of notch 172. Cam roller 162 is positioned in the narrow part of opening 160 and at the rear of clutch means 150. Spring-biased wedge pin 164 maintains the cam roller 162 toward the rear end of clutch mechanism 150. During the forward stroke of thrust bar 158, the surface of cam roller 162 contacts base 176 of notch 172 and inclined surface 156, and is rotated by the movement of thrust bar 158. At the same time, cam roller 162 bears against spring-biased wedge 164 which restrains the longitudinal forward movement of cam roller 162 so that the cam roller is kept in the narrow part of opening 160. An attempted return movement of thrust bar 158 to its initial position from its partially advanced position would cause cam roller to rotate in a counterclockwise direction. This movement would be prevented by clutch mechanism 150, however, since counterclockwise rotation of cam roller 162 causes cam roller 162 to "lock" itself between thrust bar 158 and inclined surface 156 of cam block 152 thereby preventing all but the slightest movement of thrust bar 158 toward its relaxed position.

Turning now to FIG. 3, clutch mechanism 150 is seen in dotted lines, with thrust bar 158 being at the forward end of its stroke. In this position, cam roller 162 has been forced to the other side of wedge pin 164 by shoulder portion 178 of notch 172 and lies in the widest region of spacing 160. Once cam roller 162 has so passed wedge 164, it is housed in an area wider than its diameter and hence is free to rotate in any direction. Accordingly, cam roller 162 permits thrust bar 158 to move rearward toward its initial position. Cam roller 162 can also be moved past wedge pin 164 by manual pivoting of trigger 18 which moves bar 180 via pin 182. Near the end of the return movement of thrust bar 158 to its initial position, cam roller 162 is moved into cut-out 174 in notch 172 and is then forced past wedge 164 by shoulder portion 179 of notch 172. Cut-out portion 174 allows cam roller 162 to be moved past wedge 164 and back to its initial position shown in FIG. 5, without "locking" before the completion of the return stroke. Further details with respect to the construction and operation of the clutch mechanism can be found in commonly assigned U.S. Pat. No. 3,819,100 which discloses substantially the same clutch mechanism, the pertinent disclosure of which patent is expressly incorporated herein by reference.

Now, the operation of the inventive stapling will be described. In its relaxed state, the instrument 10 appears as illustrated in FIG. 2. The instrument is actuated by squeezing the trigger 16 toward handle 14. At the end of the first stage of operation, when the jaws of the staple-carrying cartridge 34 are completely closed, the instrument takes the position illustrated in FIG. 6. At the end of the stapling operation, and after the knife has divided the vessel under operation, the instrument takes the position illustrated in FIGS. 3 and 7. This entire operation is initiated by actuating the trigger 16 which acts on the knife rod 28 and pusher and wrap sleeves 30 and 32, respectively, through a unique driving configuration.

Upon initial actuation of the trigger 16, the rollers 48 act in the recess 50 of the rear link 52 to rotate the rear link 52 in a clockwise direction about its mounting pin 54. As will be recalled, the rollers 48 are attached to the bell crank 44 of the trigger 16. Clockwise rotation of the rear link 52 causes the thrust block 60 to move in the direction of arrow 140 through the action of the forward link 56 pivoted to the rear link 52 at 58 and pivoted to the thrust block 60 and 62. Movement of the thrust block 60 in the direction of arrow 140 is against the bias of return spring 76. During the initial movement in the direction of arrow 140, knife rod 28, pusher sleeve 30 and wrap sleeve 32 move together with their associated saddles 20, 22 and 24, respectively. Movement of the thrust block 60 is translated directly to the pusher sleeve 30 through the means of retainer 64 illustrated in FIG. 2.

From the relaxed position illustrated in FIG. 2 to just before the position illustrated in FIG. 6, the shifter dogs 124 are positioned within the respective windows 126 in the wrap sleeve 32 and project into channel 108 of the pusher sleeve 30. Accordingly, with the shifter dogs in this position, the pusher sleeve 30 integral with the thrust block 60 moves wrap sleeve 32 in the direction of arrow 140. Saddle 20, integral with knife rod 28, is also carried with the pusher sleeve 30. Such unified motion continues until the shifter dogs 124, windows 126 and channel 108 move into alignment with channel 116 in main body 12. Simultaneously, saddle 24 of the wrap sleeve 32 contacts the nose 136 of the stop mechanism 132. At this time, shifter dogs 124 slide out of channel 108 and enter channel 116. It should be understood, however, that the shifter dogs 124 are at all times at least partially positioned within their respective windows 126. With shifter dogs 124 bridging windows 126 and channel 116, the wrap sleeve 32 is held fixed relative to the main body 12 and the pusher sleeve 30 and knife rod 28 are free to continue to move with the thrust block 60 in the direction of arrow 140. As illustrated in FIG. 6, saddle 22 with its associated pusher sleeve 30, and saddle 20 with its associated knife rod 28, have moved away from saddle 24 and its associated wrap sleeve 32, now fixed relative to the main body 12.

Continued squeezing of the trigger 16 toward the handle 14 further rotates the rear link 52 in a clockwise direction about its pin 54 and drives the thrust block 60 further to the direction of arrow 140 through the means of forward link 56. During this movement, cam follower 88 rides along the cam surfaces 53 on the rear link 52. Accordingly, the knife actuating lever 80 is made to pivot in a counterclockwise direction about its pin 82. It should be noted that while the lever 80 is rotating in a counterclockwise direction, the follower 92 integral with the saddle 20 and knife rod 28 moves with the thrust block 60 in the direction of arrow 140. The action of the linkage developed by forward link 56 and rear link 52, acting through thrust block 60 and cam follower 88, results in the thrust block 60 moving in a direction of arrow 140 faster, during the initial stages of operation, than the knife actuating lever 80.

At the completion of the suturing operation, the pin 58 between the rear link 52 and the forward link 56 is in a position such as that illustrated at 58' in FIG. 7. In this position, while not shown, the contact pad 86 on the knife actuating lever 80 is rapidly approaching the rear surface of follower 92. It should be noted that from the relaxed position of the rear and forward links 52 and 56, respectively, when the common pin 58 is in the position illustrated in FIG. 2, to a position wherein the common pin 58 is as illustrated in FIG. 7 at 58', the thrust block 60 has been made to move a greater distance in the direction of arrow 140 than the knife actuating lever 80 has moved with its contact pad 86. However, from the pin position represented in FIG. 7 at 58' to the pin 58 position shown in solid lines, the contact pad 86 moves a distance far greater than that which is moved by the thrust block 60. Accordingly, the saddle 20 is driven away from the saddle 22. In the cartridge, this operation corresponds to the knife being driven forwardly to divide the already sutured vessel. FIG. 7 illustrates the instrument at the end of the dividing operation.

When a cartridge 34 is associated with instrument 10, the stroke of saddle 22 is limited to slightly less (e.g., 0.030 inch) than that shown in FIG. 7. This stroke limitation is absorbed by the collapse of Belleville washers 68 as retainer 64 is moved toward the rear of the instrument by pushers sleeve 32. The collapse of the Belleville washers builds up sufficient force to insure uniform crimping of the staples during the suturing operation.

The operation of the instrument from the position shown in FIG. 7 back to the relaxed position illustrated in FIG. 2 is as follows. When the surgeon releases the trigger 16, the thrust block 60 is moved back to the position illustrated in FIG. 2 by the bias of return spring 76. At the same time, knife return spring 98 moves saddle 20 against saddle 22. Spring 84 ensures that the knife actuating lever 80 pivots away from the follower 92, and that the cam follower pins 90 ride along pivoting cam surface 53. When the instrument returns to the orientation illustrated in FIG. 6, the shifter dogs 124 leave channel 116 and shift into channel 108. This movement of shifter dogs 124 couples the pusher sleeve 30, which is fixed to thrust block 60, with the wrap sleeve 32, thereby returning the wrap sleeve 32 to its relaxed position. When the instrument returns to the orientation illustrated in FIG. 2, it is in readiness for another operating cycle.

Above, there has been described an instrument for associating with a cartridge for ligating, suturing and dividing an organic tubular structure. It should be appreciated, however, that the above description is given for purposes of illustration only and that a number of modifications and alterations may be practiced by those skilled in the art without departing from the spirit or scope of the invention. It is the intent, therefore, that the invention not be limited to the above but be limited only as defined in the appended claims.

What is claimed is:

1. A surgical instrument adapted to associate with and operate a staple-carrying cartridge having a three-stage operation and including means for ligating an organic tubular structure in a first stage of said operation, means for suturing said structure in a second stage of said operation and means for dividing said structure in a third stage of said operation, the instrument comprising: a main body portion; first, second and third attachment means associated with said main body portion and moveable with respect to said main body portion and with respect to one another to power said three-stage operation of said staple-carrying cartridge, said first attachment means adapted to associate with said dividing means, said second attachment means adapted to associate with said suturing means and said third attachment means adapted to associate with said ligating means; trigger means moveably mounted on said main body portion; linking means operatively connecting said trigger means to said second attachment means so that actuation of said trigger means causes said second attachment means to move relative to said main body portion to cause said structure to be sutured during said second-stage of said operation; coupling means associated with said second and third attachment means for coupling said third attachment means to said second attachment means and for causing said third attachment means to move relative to said main body portion during said first-stage of said operation for ligating said structure; and means operatively connecting said trigger means to said first attachment means so that actuation of said trigger means causes said first attachment means to move relative to said third attachment means during said third-stage of said operation for dividing said structure.

2. The surgical instrument recited in claim 1, wherein at least a portion of each of said first, second and third attachment means lies, at rest, outside said main body portion; and further comprising second sleeve means integral with said second attachment means extending from said second attachment means toward the rear of said surgical instrument and into association with said linking means.

3. The surgical instrument recited in claim 2, and further comprising third sleeve means integral with said third attachment means extending from said third attachment means toward the rear of said surgical instrument and being in the form of a hollow sleeve extending about and slidably mounted with respect to said second sleeve means.

4. The surgical instrument recited in claim 2, wherein said second sleeve means is in the form of a hollow tube and said first attachment means has first rod means extending through and slidably mounted with respect to said second sleeve means.

5. The surgical instrument recited in claim 4, wherein said first, second and third attachment means are respectively, farthest from, intermediate and nearest said main body portion.

6. The surgical instrument recited in claim 5, and further comprising return biasing means for biasing said second attachment means toward said main body portion.

7. The surgical instrument recited in claim 6, wherein said return biasing means surrounds said second sleeve means and is retained, under compression, between an inner wall of said main body portion and a thrust block integral with said second sleeve means.

8. The surgical instrument recited in claim 5, and further comprising biasing means for biasing said first attachment means toward said second attachment means.

9. The surgical instrument recited in claim 8, wherein said biasing means surrounds said first rod means and is retained, under compression, between the rear portion of said first rod means and the rear portion of a thrust block integral with said second sleeve means.

10. The surgical instrument recited in claim 1, and further comprising coupling means associated with said third attachment means and with said main body portion for coupling said third attachment means to said main body portion during said second-stage and said third-stage of said operation.

11. The surgical instrument recited in claim 10, wherein said coupling means associated with said second and third attachment means couple together said second and third attachment means during said first-stage of said operation.

12. The surgical instrument recited in claim 11, wherein said coupling means comprises at least one dog mounted to move with said third attachment means, and first and second annular channels associated, respectively, with said second attachment means and said main body portion, said at least one dog serving to alternately couple said third attachment means to said second attachment means and said main body portion, respectively, by moving into said first and second annular channels.

13. The surgical instrument recited in claim 1, wherein said linking means comprises first and second link members, said first link member being pivotally mounted at one end thereof relative to said main body portion and at the other end thereof to said second link member, said second link member being associated at the end remote from said first link member with said second attachment means, and wherein said trigger means is pivotally associated with said first and second link members adjacent the juncture therebetween.

14. The surgical instrument recited in claim 1, and further comprising a stop means integral with said main body portion for limiting the movement of said third attachment means away from said main body portion.

15. The surgical instrument recited in claim 1, and further comprising clutch means for ensuring the completion of the three-stage operation once the first stage of operation is commenced.

16. The surgical instrument recited in claim 1, wherein said means for operatively connecting said trigger means to said second attachment means comprises an actuating lever pivotally mounted relative to said main body portion and having a first surface for associating with said second attachment means and a second surface spaced from said first surface for associating with said trigger means.

17. A surgical instrument adapted to associate with and operate a staple-carrying cartridge having a three-stage operation and including means for ligating an organic tubular structure in a first stage of said operation, means for suturing said structure in a second stage of said operation and means for dividing said structure in a third stage of said operation, the instrument comprising: a main body portion; first, second and third attachment means associated with said main body portion and moveable with respect to said main body portion and with respect to one another to power said three-stage operation of said staple-carrying cartridge, said first attachment means adapted to associate with said dividing means, said second attachment means adapted to associate with said suturing means and said third attachment means adapted to associate with said ligating means; trigger means moveably mounted on said main body portion; linking means operatively connecting said trigger means to said second attachment means so that actuation of said trigger means causes said second attachment means to move relative to said main body portion to cause said structure to be sutured during said second-stage of said operation; coupling means associated with said second and third attachment means for coupling said third attachment means to said second attachment means and for causing said third attachment means to move relative to said main body portion during said first-stage of said operation for ligating said structure; said coupling means also being associated with said main body portion for coupling said third attachment means to said main body portion and for causing said third attachment means to remain stationary relative to said main body portion during said second-stage and said third-stage of said operation; and means operatively connecting said trigger means to said first attachment means so that actuation of said trigger means causes said first attachment means to move relative to said third attachment means during said third-stage of said operation for dividing said structure.

18. The surgical instrument recited in claim 17, wherein said first, second and third attachment means are respectively, farthest from, intermediate and nearest said main body portion.

19. The surgical instrument recited in claim 17, wherein said coupling means comprises at least one dog mounted to move with said third attachment means, and first and second annular channels associated, respectively, with said second attachment means and said main body portion, said at least one dog serving to alternately couple said third attachment means to said second attachment means and said main body portion, respectively, by moving into said first and second annular channels respectively.

20. The surgical instrument recited in claim 17, and further comprising a stop means integral with said main body portion.

* * * * *